(12) United States Patent
Cybulski et al.

(10) Patent No.: US 7,540,681 B2
(45) Date of Patent: Jun. 2, 2009

(54) SURGICAL PREP SOLUTION APPLICATOR

(75) Inventors: Claude E. Cybulski, Lake Elmo, MN (US); Eric R. Cybulski, Woodbury, MN (US); Brook F. Duerr, Lake Elmo, MN (US); Kent E. Lageson, Burnsville, MN (US); Steven E. Turch, Blaine, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/958,444

(22) Filed: Oct. 4, 2004

(65) Prior Publication Data

US 2006/0072962 A1   Apr. 6, 2006

(51) Int. Cl.
B05C 21/00  (2006.01)
(52) U.S. Cl. ...................... 401/205; 401/133
(58) Field of Classification Search ......... 401/196–207, 401/133
See application file for complete search history.

(56) References Cited

U.S. PATENT DOCUMENTS

| | | | |
|---|---|---|---|
| 2,932,277 A * | 4/1960 | Borah | 118/270 |
| 3,355,240 A | 11/1967 | Schwartzman | 401/205 |
| 3,410,645 A * | 11/1968 | Schwartzman | 401/135 |
| 3,468,611 A * | 9/1969 | Ward | 401/186 |
| 4,498,796 A * | 2/1985 | Gordon et al. | 401/132 |
| 4,507,111 A * | 3/1985 | Gordon et al. | 604/3 |
| 4,542,012 A | 9/1985 | Dell | 424/28 |
| 4,584,192 A | 4/1986 | Dell et al. | 424/81 |
| 4,762,433 A * | 8/1988 | Bergeson et al. | 401/206 |
| 4,925,327 A | 5/1990 | Wirt | 401/205 |
| 5,070,552 A * | 12/1991 | Gentry et al. | 4/615 |
| 5,288,159 A | 2/1994 | Wirt | 401/133 |
| 5,308,180 A | 5/1994 | Pournoor et al. | 401/205 |
| D351,229 S | 10/1994 | Wirt | D24/119 |
| 5,435,660 A | 7/1995 | Wirt | 401/135 |
| 5,658,084 A | 8/1997 | Wirt | 401/132 |
| 6,099,184 A * | 8/2000 | Koptis | 401/190 |
| 6,190,367 B1 | 2/2001 | Hall | 604/290 |
| 6,334,727 B1 * | 1/2002 | Gueret | 401/47 |
| 6,422,778 B2 | 7/2002 | Baumann et al. | 401/266 |
| 6,672,784 B2 | 1/2004 | Baumann et al. | 401/266 |
| 2002/0197228 A1 | 12/2002 | LaSala et al. | 242/70 |
| 2004/0068218 A1 | 4/2004 | Davis et al. | 604/2 |
| 2004/0114988 A1 | 6/2004 | Baumann et al. | 401/266 |
| 2004/0228670 A1 | 11/2004 | Colburn et al. | 401/11 |
| 2005/0135867 A1* | 6/2005 | Gueret | 401/205 |

* cited by examiner

*Primary Examiner*—David J Walczak
(74) *Attorney, Agent, or Firm*—Nancy M. Lambert

(57) ABSTRACT

Systems and methods for applying or dispensing fluids such as surgical prep solution. The applicator includes a distributor element and a container of surgical prep solution. The distributor element includes a projecting element that separates at least two orifices in the distributor element to provide uniform distribution of the surgical prep solution.

37 Claims, 6 Drawing Sheets

SURGICAL PREP SOLUTION APPLICATOR

BACKGROUND OF THE INVENTION

Antiseptic preparation of patients for surgery conventionally includes a 3-10 minute scrubbing of the affected area with a soap solution followed by the application of a water-soluble antiseptic paint solution.

Over the years, devices have been developed in an attempt to control solution delivery, and to reduce the time required for application of antiseptic solutions. In particular, the Duraprep™ products commercially available from 3M Company of St. Paul, Minn. have enjoyed commercial success by providing controlled, convenient application.

Coassigned U.S. Pat. No. 4,925,327, describes a liquid applicator that incorporates a rigid, porous metering insert to regulate the flow rate of liquid disposed between the applicator hollow elongate member and a foam sponge covering a major orifice of the hollow elongate member. The liquid to be dispensed is contained in a rupturable reservoir removably affixed at the other major orifice of the hollow elongate member. Coassigned U.S. Pat. No. 5,658,084, further discloses a liquid applicator where the liquid is contained in a frangible ampoule inside the body of the applicator. This ampoule is supported and protected by a deformable element that prevents unintentional breakage of the ampoule from impacts during storage and handling before use. The applicator is actuated by pushing at least a portion of the frangible ampoule through an aperture in the deformable element and into contact with a means for breaking the ampoule. Coassigned U.S. Pat. No. 6,672,784 describes an applicator system including a distributor element and a collapsible container of surgical prep solution.

While these products have provided a considerable advance, applicators that provide more uniform fluid delivery and/or increased speed of fluid delivery are needed.

SUMMARY OF THE INVENTION

The present invention provides an applicator useful as an applicator for the application of fluids to a surface comprising comprising a hollow elongate member comprising a container; a flange extending radially outward from said hollow elongate member; and distributor element attached to the flange, the distributor element comprising: a first side and a second side; at least two orifices; at least one projecting element rising from the first side of the distributor element; wherein the projecting element is proximate the center and separates the at least two orifices; and an absorbent pad attached to the first side of the distributor element.

In a preferred embodiment, the distributor element comprises at least four orifices. In some embodiments, the projecting element comprises a raised area proximate the center of the distributor element, such as a raised platform. In most embodiments, the projecting element comprises at least one rib projecting from the first side of the distributor element. The projecting element may further comprise a series of interconnecting ribs that form chambers on the first side of the distributor element.

The embodiments of the present invention provide a means to reliably deliver in a short period of time a surgical prep solution to the applicator sponge and uniformly distribute the prep solution throughout the applicator sponge. The applicator controls the flow rate of fluid to the applicator sponge and fluid distribution within the sponge without the need for external operator manipulation such as squeezing the liquid container or compressing the applicator sponge against an external surface. Although intended to apply modern, low viscosity, non-water-soluble, film-forming prep solutions, this device can be configured to apply a variety of solution compositions, viscosities, densities and volumes without compromising the fast wetting and uniform distribution features.

BRIEF DESCRIPTION OF THE DRAWINGS

A more complete understanding of the invention and its advantages will be apparent from the Detailed Description taken in conjunction with the accompanying Drawings, in which.

DETAILED DESCRIPTION

Figure 1:
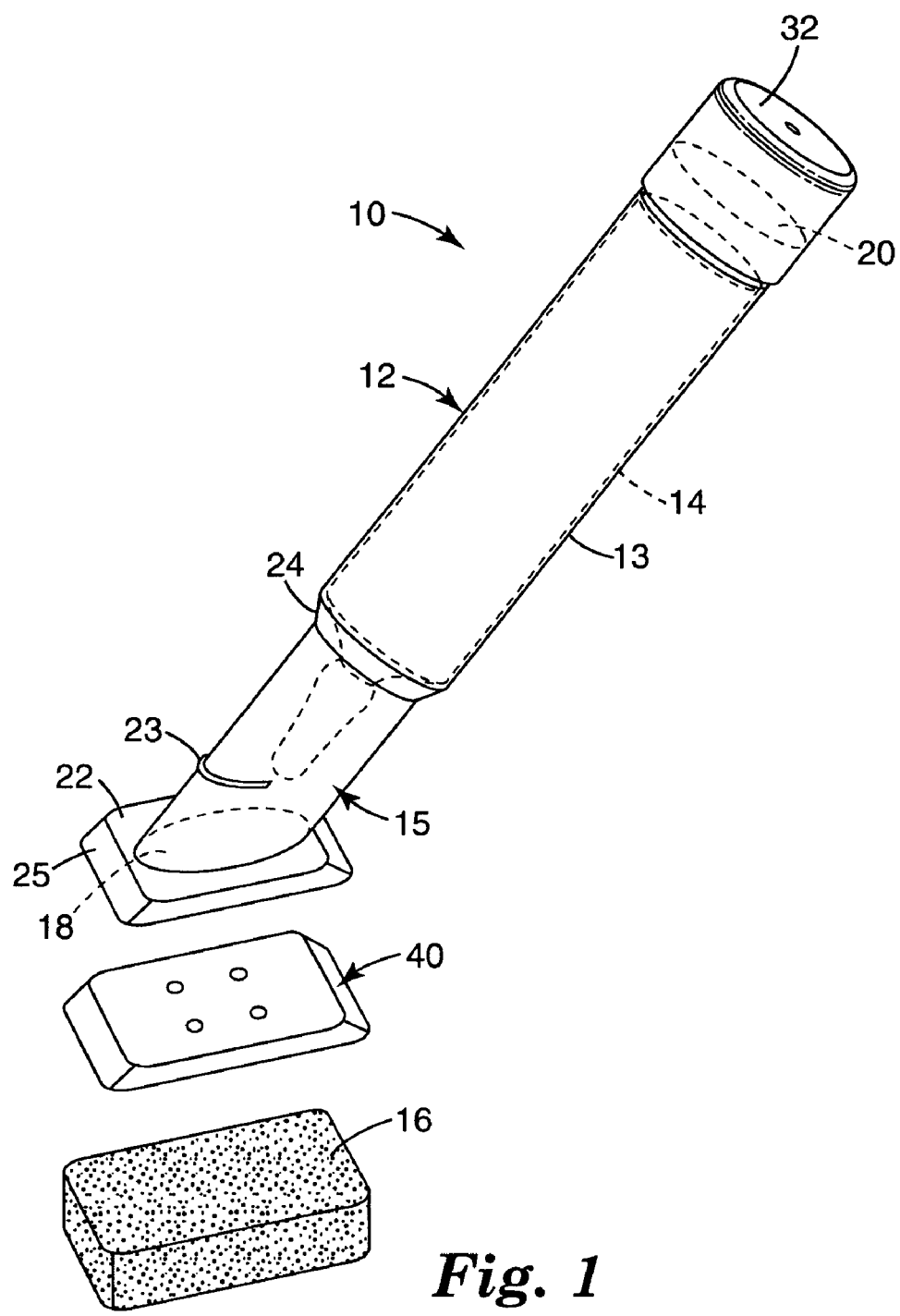
FIG. 1 is an exploded perspective view of one illustrative embodiment of an applicator of this invention.

FIG. 1 is an illustrative embodiment of a fluid applicator that includes many aspects of the applicator of the present invention. It should, however, be understood that all of the features depicted in the applicator of FIG. 1 need not necessarily be present in all applicators according to the present invention. In other words, the features of the applicator depicted in FIG. 1 may be used in concert or various combinations of the features may be employed to achieve some of the advantages possible in light of the present invention.

Referring to FIG. 1, one embodiment of a surgical prep applicator is provided. The applicator 10 comprises a hollow elongate member 12 which can serve as a handle, a flange 22 connected to the hollow elongate member 12, and a distributor element 40 connected to the flange 22 on the side opposite the hollow elongate member 12. An absorbent pad 16 is attached to the distributor element. The hollow elongate member 12 is in fluid communication with the flange 22 through first major orifice 18.

As shown in FIG. 1, absorbent pad 16 preferably, but not necessarily, is larger than the base of hollow elongate member 12. This arrangement allows for soft edges and also facilitates prepping between digits of the human hand or other narrow prepping surfaces. While shown as a square, absorbent pad 16 may be of any shape that makes fluid application convenient. Shapes such as rectangles, ellipses, circles, triangles, ovals, etc., are contemplated.

The hollow elongate member is any molded plastic piece about 10-20 cm, preferably about 15 cm in length having an attachment means for the pad at the base. Preferably, the hollow elongate member and distributor element are integrally formed, such as by injection molding processes. The base portion of the hollow elongate member is preferably at an angle of 45 degrees to the axis of the hollow elongate member.

With reference to the embodiment depicted in FIG. 1, the applicator 10 includes a hollow elongate member 12 adapted to support a container 14. One form of a container 14 includes a frangible ampoule containing the solution to be applied by the applicator 10. The hollow elongate member 12 acts as a handle and as a fluid container after the ampoule has been broken, but before the solution is dispensed by the absorbent pad 16. The hollow elongate member 12 is bounded by a first major orifice 18 and second major orifice 20, one at each end. A flange 22 adapted to accept the distributor element 40 and/or the absorbent pad 16 surrounds the first orifice 18. In alternate less preferred embodiments, the distributor element 40 attaches directly to the hollow elongate member 12 and disposed over the first major orifice 18 (i.e., there is no flange 22). Internally, the hollow elongate member 12 is conveniently constructed to include a collar (not shown) which serves as a preferred deformable means for supporting and protecting the ampoule until the applicator 10 is to be used. An example of a hollow elongate member with a frangible ampoule for delivering surgical prep solution is further described and shown in FIGS. 1 to 6 of U.S. Pat. No. 5,658,084. Other suitable configurations for the applicator include those described in U.S. Pat. Nos. 5,288,159 and 5,435,660.

The container 14 should form a barrier to materials and methods used in sterilization such as ethylene oxide gas, irradiation methods, and hydrogen peroxide. Alternate embodiments to a frangible ampoule for delivering the surgical prep solution include collapsible containers such as those decribed in U.S. Pat. No. 6,422,778 or the pierceable container as described in Published Application No. 2004/0068218. The container may, for example, be provided in a tube resembling a toothpaste tube. It may be preferred that the container is rigid enough to act as a hollow elongate member for the applicator system. The container may be collapsible and compression of the container causes the surgical prep solution to flow from the container to the absorbent pad.

The absorbent pad 16 can be selected from a variety of commercially available materials having a wide range of compression set ratios, densities and porosities. For a given volume, viscosity, density and surface tension of the liquid, wetting of the absorbent pad can be accomplished by appropriate specification of the average pore size, pore size distribution, void volume fraction and surface energy of the material from which the absorbent pad 16 is formed, and the permanent compression set ratio and porosity of the open-cell absorbent pad 16. The compression state (i.e., compressed or uncompressed) and porosity of the foam sponge are adjusted in relation to the viscosity, density, volume and surface tension of the liquid to be dispensed to allow a portion of the liquid contained in the applicator to flow to the outer surface of the foam sponge.

The absorbent pad 16 comprises a foam material compatible with the liquid to be dispensed. Suitable foam sponge materials are prepared from thermoplastic materials such as polyethylene and polyurethane. Especially preferred open-cell foam materials are prepared from polyurethane thermoplastics. The foam material can be reticulated (open cell) or non-reticulated (closed cell) foam. The foam material can also be compressed (felted) or uncompressed. Preferably, the foam material is reticulated and uncompressed.

Many other materials for the absorbent pad may be possible, including non-woven carded webs, filter material, knit pads, such as gauze, woven pads, and the like. These pads can be made from synthetic or natural polymers. It is also contemplated in the present invention that an additional layer of a fabric may be placed over the absorbent pad. Such additional fabrics may aid in coating uniformity.

The selection of the foam material will also affect wicking and reservoiring properties of the foam sponge. The foam material can also affect the coating characteristics of the applicator. Preferably, for surgical prep applications, the porosity of the foam sponge material is between 4 and 40 pores per linear centimeter, more preferably about 35 pores per linear centimeter. A particularly preferred open-cell foam sponge material is an elastomeric polyurethane foam having a porosity of about 35 pores per linear centimeter, commercially available from Foamex, LP, East Providence, R.I. as "Z90CLB".

The absorbent pad 16 is attached to the distributor element 40 by a seal formed between the absorbent pad and a projecting element (i.e., ribs and/or platforms described further below) on the distributor element. The seal between the absorbent pad and the projecting element may be formed by any suitable bonding techniques known in the art such as adhesives, hot plate welding, solvent bonding, ultrasonic welding, inductive welding, and plastic rod welding. In a preferred embodiment, the absorbent pad is attached to the projecting element to form a seal by hot plate welding.

The distribution and rate of delivery of the liquid to the absorbent pad 16 is also controlled by the orifice size, orifice locations, orifice shape, number of orifices, types and form of the chambers formed by the projecting element, as well as the material specifications of the absorbent pad 16. In preferred embodiments, the orifice size is at least 0.0025 centimeters, and more preferably at least 0.025 centimeters. In most embodiments, the orifice size is less than 0.635 centimeters, and more preferably less than 0.625 centimeters.

Figure 2:
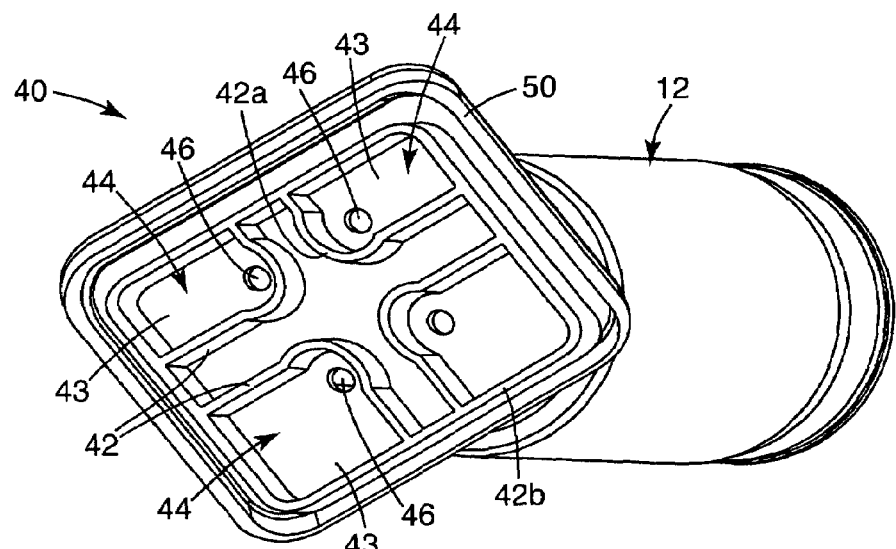
FIG. 2 is a perspective view of one illustrative embodiment of an applicator showing the distributor element without the sponge.

The invention will now be more particularly described in terms of the following particularly preferred embodiment. Referring to FIGS. 1-2, the applicator 10 consists of the following components: a container 14 comprising a frangible ampoule containing the solution to be dispensed; a hollow elongate member 12 adapted to accept the container 14, and having a flange 22 surrounding a first orifice 18; a cap 32 positioned over the second major orifice 20 of the hollow elongate member 12; a distributor element 40 disposed within the flange 22 of the hollow elongate member 12; and an absorbent pad 16 disposed over the distributor element 40.

The hollow elongate member 12 can be molded from any thermoplastic material compatible with the liquid to be dispensed. Preferably, the hollow elongate member 12 is molded from high density polyethylene. Features of the preferred embodiment of this component include a tubular handle portion 13, a dispensing portion 15, a first major orifice 18 with an integrally formed radially-projecting surrounding flange 22 adapted to accept the distributor element 40, a second major orifice 20 adapted to retain a cap 32, and a shoulder 24 disposed between the first orifice 18 and second orifice 20 adapted to support a collar.

For surgical prep applications, it is important that the hollow elongate member 12 be long enough to prevent contact of the patient by the person applying the surgical prep solution. Preferably, for such applications the hollow elongate member is at least four inches long. In the preferred embodiment, the tubular handle portion 13 of the hollow elongate member has a larger diameter than the dispensing portion 15.

Integrally-formed flange 22 surrounds the first orifice 18 and is angled from the longitudinal axis of the hollow elongate member 12 by between 30 and 90 degrees in most embodiments. Most preferably, there is about a 45 degree angle between the flange 22 and the longitudinal axis of the hollow elongate member 12.

For surgical prep applications, the applicator may also include an indicator line 23 as shown in FIG. 1. The indicator line provides an indication to the user that the surgical prep has at least partially filled the absorbent pad 16, and that the applicator is ready to apply solution to the patient.

In a preferred embodiment, a cap 32 covers the second major orifice 20 of the hollow elongate member 12. A suitable configuration for the cap is further described in U.S. Pat. No. 5,658,084. The cap 32 is adapted to transmit an actuation force to the container 14 as the cap is axially displaced in the direction towards absorbent pad 16, in order to release the surgical prep solution from the container 14 to the dispensing portion 15.

In a preferred embodiment, as shown in FIG. 2, the distributor element 40 comprises at least one projecting element rising from the surface 43 of the distributor element 40. In FIG. 2, the projecting element is a series of interconnected ribs 42 comprising interior rib 42a and exterior rib 42b. The ribs 42 form chambers 44 around the orifices 46 to create a orifice-free zone 48 proximate the center of the distributor element 40.

The orifice-free zone 48 created by the ribs 42 allows more uniform distribution of the surgical prep solution as the solution enters the absorbent pad 16. The surgical prep liquid is delivered to the applicator absorbent pad 16 which is applied over the surgical field to disinfect it. The ability to apply a controlled uniform coat allows application of the liquid to only the desired areas of the patient, and promotes efficacy of the surgical prep. The orifice-free zone of the distributor element avoids concentrating the fluid in the center of the absorbent pad as the fluid flows through the orifices.

Figure 3:
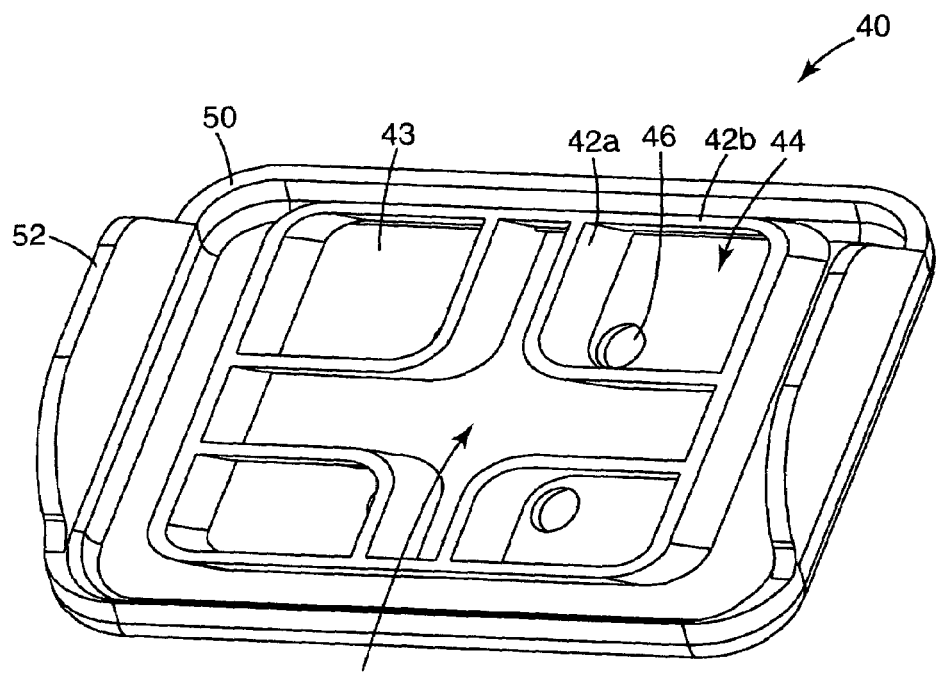
FIG. 3 is a perspective view of one illustrative embodiment of a distributor element.

As further shown in FIG. 3, the ribs surrounding the orifice can be straight or curved and may be of any thickness. In a preferred embodiment, the ribs have a thickness of at least 0.75 cm, more preferably at least 0.125 cm.

Referring again to FIG. 2, the distributor element also comprises an edge 50 that projects from the perimeter of the distributor element. The edge 50 provides a support for the absorbent pad 16 and can add in the aesthetic appearance of the applicator during use. Without the outer edge, a gap can form between the surface of the distributor element and the side of the absorbent pad 16 attached to the distributor element. As shown in FIG. 3, the edge 50 may also form a raised edge 52 on one or more sides or the distributor element perimeter. The raised edge 52 can aid in limiting the compression of the absorbent pad during use.

In preferred embodiments, exterior rib 42b runs along the perimeter adjacent the edge 50. The exterior rib 42b can assist in the manufacture of the distributor element, such as the hot weld process as described in Examples. While not required, the ribs 42 typically project from the surface of the distributor element to a height higher from the surface than the edge 50.

As further shown in FIG. 3, the ribs 42 and edge 50 project from the surface of the distributor element 40 at angles of 45° and 90°. The ribs 42 and edge 50 can project at any angle from the surface 43 depending on the application and the manufacturing processes employed to form the distributor element 40.

Figure 4:
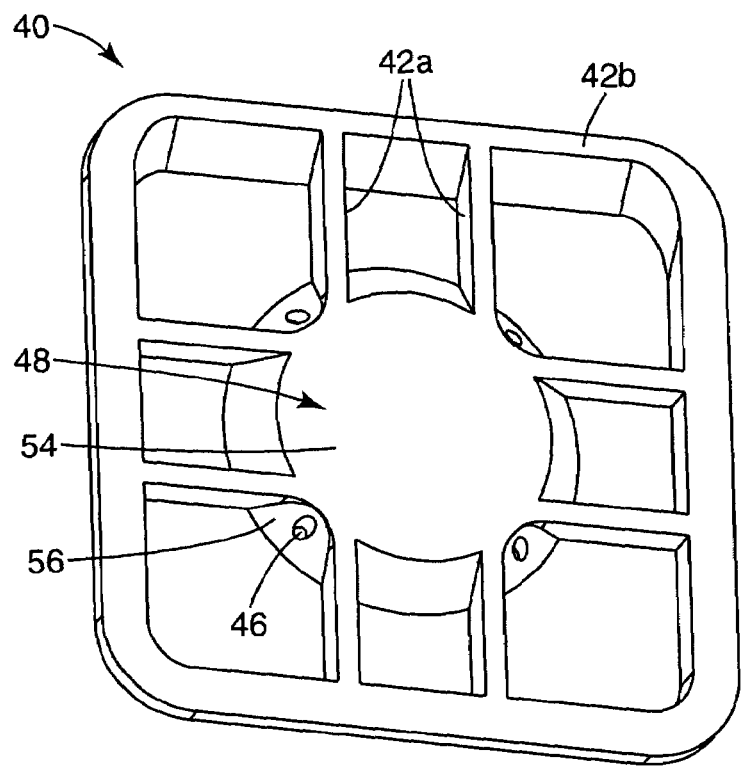
FIG. 4 is a perspective view of another illustrative embodiment of a distributor element.
Figure 5:
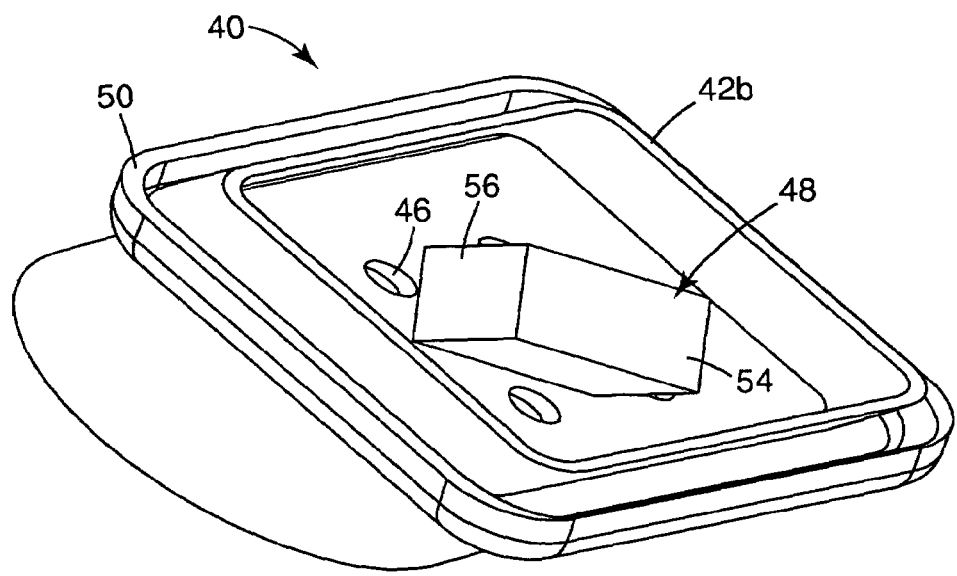
FIG. 5 is a perspective view of another illustrative embodiment of a distributor element.
Figure 6:
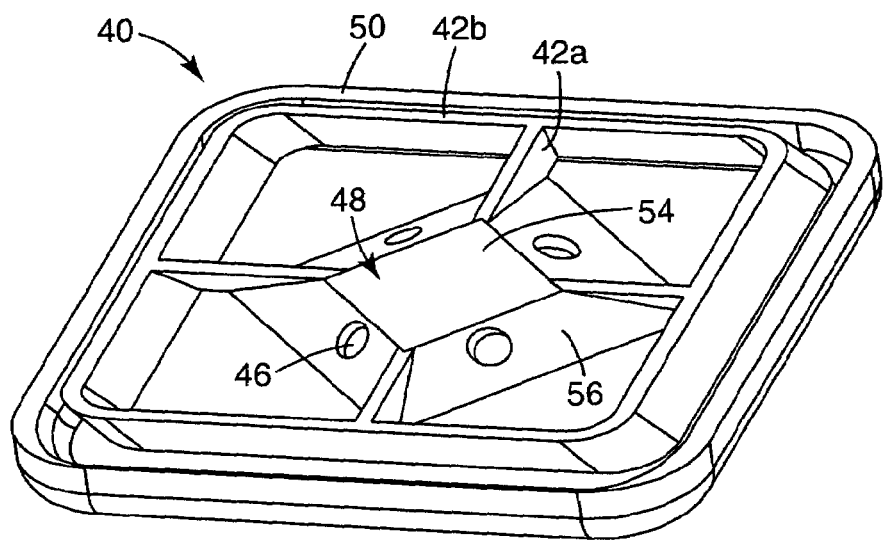
FIG. 6 is a perspective view of another illustrative embodiment of a distributor element.
Figure 9:
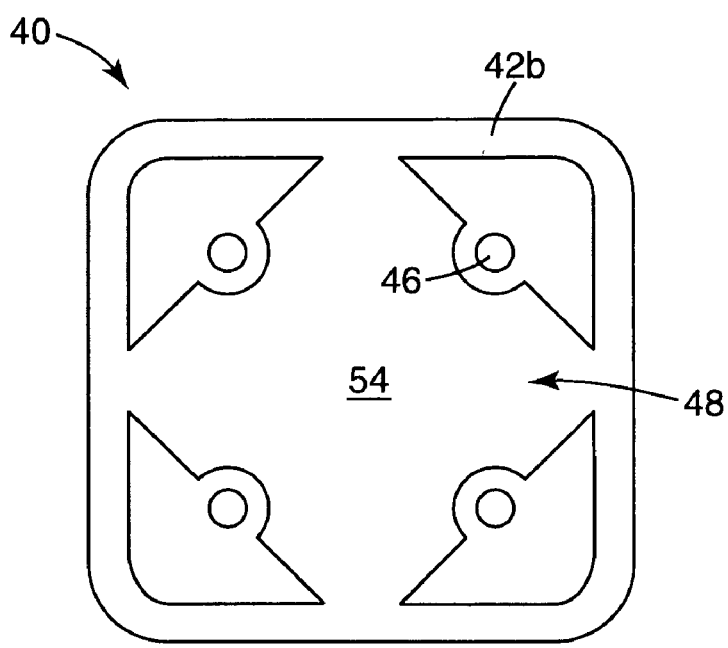
FIG. 9 is a plan view of one illustrative embodiment of the distributor element.

In another embodiment shown in FIG. 4, the orifice-free zone 48 proximate the center of the distributor element 40 can comprise a projecting element that forms a raised platform 54. The raised platform 54 can be any shape, shown as a truncated cone platform in FIG. 4, or a raised platform 54 in the form of a cube or other boxlike structure as shown in FIGS. 5 and 9, or a truncated pyramid as shown in FIG. 6. In a preferred embodiment, the orifices 46 are located adjacent the raised platform (i.e., the orifices are not located in or on the raised platform) as shown in the embodiment of FIG. 5. In alternate embodiments, as shown in FIGS. 4 and 6, the raised platform can consist of angled sides 56 extending down to the surface 43 of the distributor element 40 wherein the angled sides 56 contain the orifices 46.

In those embodiments comprising a raised platform 54, ribs 42 may also be used to form a chamber around the orifices 46. In FIGS. 4 and 6, the interior ribs extend from the raised platform to the exterior rib 42b. In other embodiments, rib 42a may not be used, as shown in FIGS. 5 and 9. In an alternate embodiment as shown in FIG. 9, the side walls of the raised platform 54 extend to the exterior rib 42b to form chambers around orifices 46.

Figure 7:
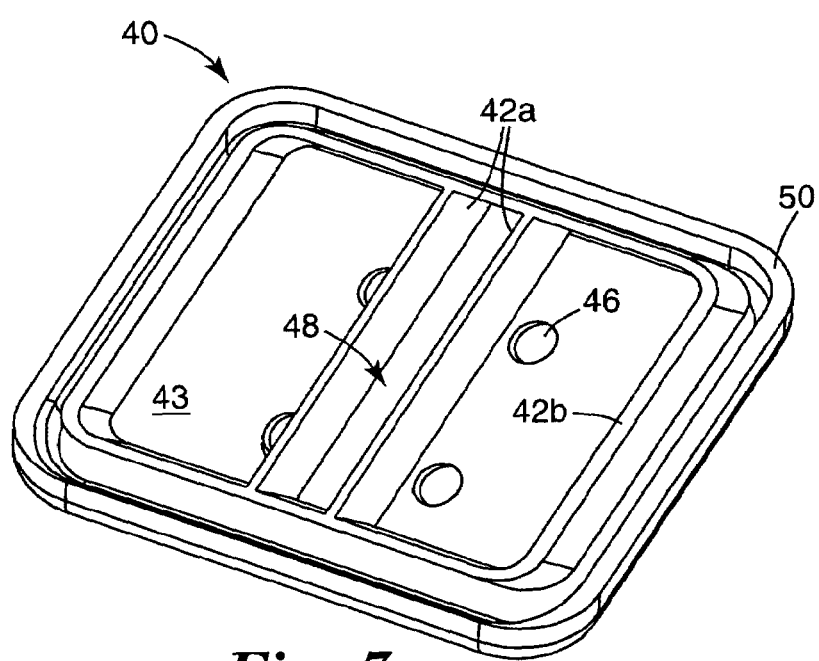
FIG. 7 is a perspective view of another illustrataive embodiment of a distributor element.
Figure 8:
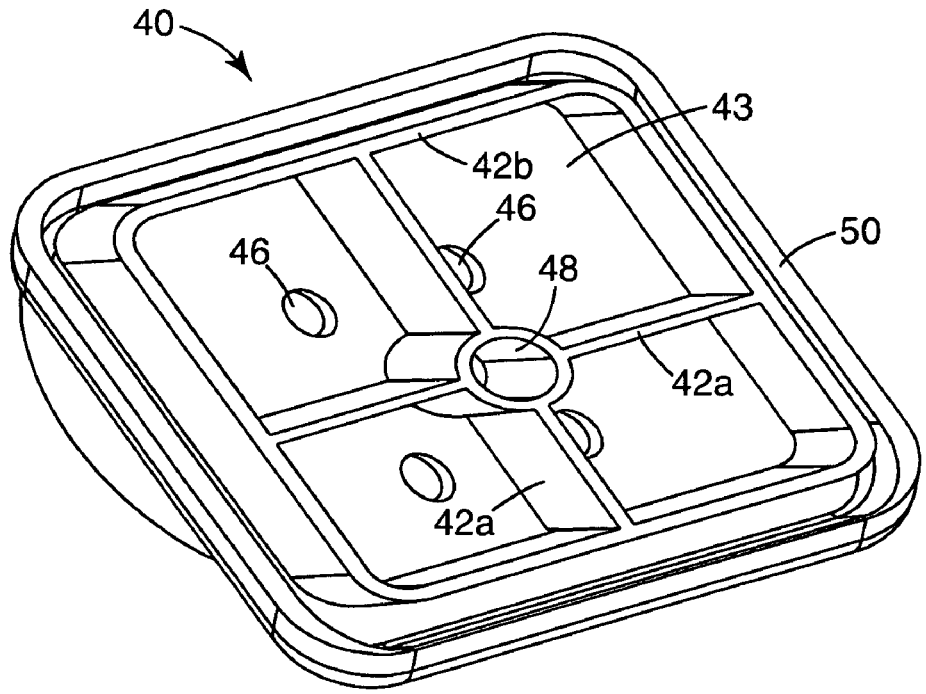
FIG. 8 is a perspective view of another illustrative embodiment of a distributor element.

As shown in FIGS. 7 and 8, other embodiments for creating an orifice free zone 48 proximate the center of the distributor element 40 are shown. In FIG. 7, two substantially parallel ribs 42a extend the width of distributor element 40. The area between the parallel ribs 42a create an orifice free zone 48. In FIG. 8, the ribs 42a form the walls of a cylindrical area that creates the orifice-free zone 48.

The distributor element 40, flange 22 and/or hollow elongate member 12 may be integrally formed in one piece such as by injection molding. In an alternate embodiment as shown in FIG. 1, the distributor element 40 may form a piece separate from the flange 22 and/or hollow elongate member 12. As shown in FIG. 1, the flange may form a flared receptacle with flange walls 25 for receiving the distributor element.

A metering film may also be used with the distributor element of the present invention. One example of a suitable metering film having a porous structure, preferably a replicated patterned structure, is described in U.S. Pat. No. 5,658,084. One type of useful flexible porous layer is a microstructured isoporous membrane having an array of pores therein, described in commonly assigned U.S. Pat. No. 5,308,180.

As noted above, the applicator is useful in dispensing antiseptic liquids to disinfect a surgical field prior to surgery. The applicator of this invention may be particularly useful in dispensing liquids having viscosities at room temperature of less than about 10,000 cps, most preferably less than about 500 cps. Examples of suitable antiseptic preparations include those described in U.S. Pat. No. 4,584,192 and those described in U.S. Pat. No. 4,542,012, the disclosures of which are incorporated herein by reference. Preferred antiseptic preparations are iodophoric skin tinctures, such as "Duraprep™ Surgical Solution," commercially available from 3M.

The containers used in connection with the present invention may also be filled with a compositions that include (as the antimicrobial agent) iodine, an iodine complex, chlorhexidine, chlorhexidine salts, or combinations thereof. Preferred iodine complexes may include iodophors, e.g., povidone-iodine USP. Preferred chlorhexidine salts may include, e.g., chlorhexidine digluconate and chlorhexidine diacetate. Other suitable antimicrobial agents may include C2-C5 lower alkyl alcohols (including, e.g., ethyl alcohol, 1-propanol, and 2-propanol), parachlorometaxylenol (PCMX), triclosan, hexachlorophene, fatty acid monoesters of glycerin and propylene glycol such as glycerol monolaurate, glycerol monocaprylate, glycerol monocaprate, propylene glycol monolaurate, propylene glycol monocaprylate, propylene glycol moncaprate, phenols, surfactants, and polymers that include a (C12-C22)hydrophobe and a quaternary ammonium group, polyquatenary amines such as polyhexamethylene biguanide, quaternary ammonium silanes, silver, silver salts (such as silver chloride), silver oxide and silver sulfadiazine, methyl, ethyl, propyl and butyl parabens, octenidene, peroxides (e.g., hydrogen peroxide and benzoyl peroxide), and the like, as well as combinations thereof.

For use in preparation for a small surgical procedure, the amount of skin antiseptic composition in the containers used in connection with the present invention should generally be able to cover an area of, e.g., 10 square centimeters or more. For larger surgical procedures, the applicator should be able to cover at least the torso of a large person, e.g., at least about 500-600 square centimeters.

While the applicators described herein are contemplated for use with surgical prep solutions, other applications may also utilize the applicator of the present invention. Other fluids for use in the applicator include, but are not limited to cleaning agents, varnishes, stains and lacquers.

Figure 10:
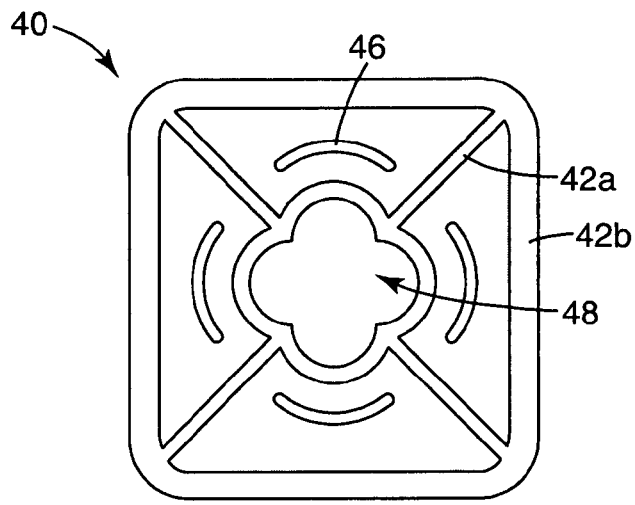
FIG. 10 is a plan view of another illustrative embodiment of the distributor element.
Figure 11:
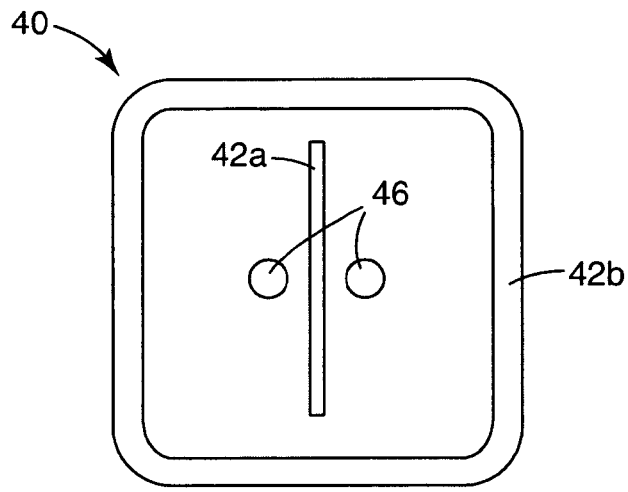
FIG. 11 is a plan view of another illustrative embodiment of the distributor element.
Figure 12:
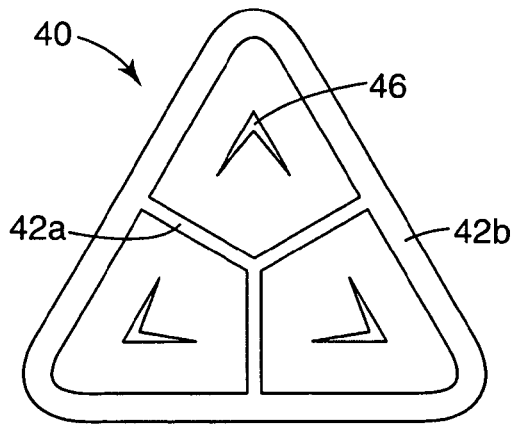
FIG. 12 is a plan view of another illustrative embodiment of the distributor element.

Alternate embodiments of the distributor element 40 are shown in FIGS. 10-12. While round orifices are utilized in most embodiments the orifices can be of any shape that provides delivery of the surgical prep solution to the absorbent pad 16. Accordingly, orifices 46 can be curved slots as shown in FIG. 10 or V-shaped slots as shonw in FIG. 12.

Other embodiments of the distributor element 40 are contemplated. The shape of the distributor element 40 and/or absorbent pad 16 can be manufactured in shapes other than square, such as the triangular distributor element 40 as shown in FIG. 12.

The ribs 42 typically are interconnected to form enclosed chambers 44 as shown in FIGS. 10 and 12. The chambers formed by junctions of interior ribs 42*a* and exterior ribs 42*b* are usually equivalent in size and prevent fluid communication between the orifices 46.

In alternate less preferred embodiments, as depicted in FIG. 11, the interior ribs 42*a* and exterior ribs 42*b* are not connected, and the orifices 46 are in fluid communication around interior rib 42*a*.

The invention is further illustrated by the following non-limiting examples.

EXAMPLES

Six identical example applicators with a distributor element generally as depicted in FIG. 2 were prepared. For each applicator, an absorbent pad, made from fully reticulated, open cell, polyester/polyurethane clickable foam having a porosity of about 35 pores per linear centimeter (commercially available from Foamex, LP, East Providence, R.I. as "Z90CLB"), was hot plate welded to the distributor element using the following general technique. A hot plate or other suitable hot surface was preheated to a temperature above the melting point of the resin used in the distributor element. The projecting elements (rib portion) of the distributor element was then placed in contact with the hot plate surface for a sufficient period of time to soften or melt the resin to a depth suitable for good surface contact with the absorbent pad. After the resin of the applicator was softened or melted sufficiently, the applicator was placed onto the absorbent pad. The melted resin of the ribs then formed a structural bond with the absorbent pad material upon cooling of the resin. During the time of welding, the exterior and interior ribs of the distributor element formed a contiguous seal with the absorbent pad. An ampoule was filled with 26 milliliters of DURAPREP Surgical Solution (commercially available from 3M, St. Paul, Minn.). After the six identical applicators were prepared, the time required for each applicator to deliver 26 milliliters of solution to the sponge after breaking the ampoule was measured for each. Results are shown in Table 1.

Six identical, comparative, applicators of DURAPREP 8630 liquid dispenser (commercially available from 3M, St. Paul, Minn.), of equivalent size to deliver 26 milliliters DURAPREP Surgical Solution, were also prepared and the time required for each applicator to deliver 26 milliliters of solution to the sponge after breaking the ampoule was measured for each. Results are shown in Table 1.

TABLE 1

| | Activation Time (seconds). | |
|---|---|---|
| | 3M 8630 DURAPREP Applicator | One Embodiment of the Present Invention |
| Trial 1 | 25.32 | 9.12 |
| Trial 2 | 27.06 | 8.90 |
| Trial 3 | 24.62 | 11.31 |
| Trial 4 | 27.31 | 9.72 |
| Trial 5 | 27.40 | 9.78 |
| Trial 6 | 25.32 | 9.12 |

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of this invention, and it should be understood that this invention is not limited to the illustrative embodiments set forth herein. Accordingly, the invention is to be limited only by the claims provided below.

Although specific embodiments of the invention have been described herein, it is not intended to limit the invention solely thereto, but to include all of the obvious variations and modifications within the spirit and scope of the appended claims.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of this invention, and it should be understood that this invention is not limited to the illustrative embodiments set forth herein. Accordingly, the invention is to be limited only by the claims provided below.

What is claimed is:

1. An applicator for dispensing a fluid, comprising:
   a hollow elongate member comprising a container;
   a flange extending radially outward from said hollow elongate member; and
   distributor element attached to the flange, the distributor element comprising:
      a first side and a second side;
      at least two orifices;
      at least one projecting element rising from the first side of the distributor element;
   and an absorbent pad attached to the projecting element;
   wherein the projecting element is proximate the center of the distributor element and separates the at least two orifices such that the at least two orifices are only in fluid communication with each other on the first side of the distributor element through the absorbent pad; and wherein the projecting element comprises an orifice-free zone that avoids concentrating the fluid in the center of the absorbent pad as the fluid flows through the orifices into the absorbent pad.

2. The applicator of claim 1, wherein the orifice size is at least 0.0025 centimeters.

3. The applicator of claim 1, wherein the orifice size is less than 0.635 centimeters.

4. The applicator of claim 1, wherein the number of orifices is at least four.

5. The applicator of claim 1, wherein the projecting element comprises a raised area proximate the center of the distributor element.

6. The applicator of claim 5, wherein the raised area is a raised platform.

7. The applicator of claim 1, wherein the projecting element comprises at least one rib projecting from the first side of the distributor element.

8. The applicator of claim 1, wherein the projecting element comprises a series of interconnecting ribs that form chambers on the first side of the distributor element.

9. The applicator of claim 8, wherein the orifices are located within the chambers.

10. The applicator of claim 8, wherein the ribs form at least one chamber free of orifices.

11. The applicator of claim 1, wherein the absorbent pad is uncompressed open-cell foam.

12. The applicator of claim 1, wherein the container is collapsible.

13. The applicator of claim 1, wherein the container holds surgical prep solution.

14. The applicator of claim 13, wherein the surgical prep solution comprises a viscosity of 500 cps or less.

15. The applicator of claim 13, wherein the surgical prep solution comprises iodine.

16. The applicator of claim 1, wherein the container is substantially impermeable to ethylene oxide gas.

17. The applicator of claim 1, wherein the absorbent pad is attached to the distributor element by a seal.

18. The applicator of claim 17, wherein the seal comprises a weld such that the pad is mechanically bonded to the distributor element.

19. An applicator for dispensing a fluid, comprising:
a hollow elongate member comprising a container;
a flange extending radially outward from said hollow elongate member; and
distributor element attached to the flange, the distributor element comprising:
a first side and a second side;
at least three chambers on the first side; and
an absorbent material attached to at least one chamber;
wherein at least two chambers each contain at least one orifice such that the at least one orifice of one chamber is only in fluid communication with the at least one orifice of the other chamber on the first side of the distributor element through the absorbent material;
wherein at least one chamber proximate the center of the distributor element is free of orifices to avoid concentrating the fluid in the center of the absorbent material as the fluid flows through the orifices into the absorbent material.

20. The applicator of claim 19, wherein the number of chambers is at least four.

21. The applicator of claim 19, wherein the orifice size is at least 0.0025 centimeters.

22. The applicator of claim 19, wherein the orifice size is less than 0.635 centimeters.

23. The applicator of claim 19, wherein the number of orifices is at least four.

24. The applicator of claim 19, wherein the chambers comprise at least one rib projecting from the first side of the distributor element.

25. The applicator of claim 19, wherein the chambers comprise a series of interconnecting ribs that form chambers on the first side of the distributor element.

26. The applicator of claim 19, wherein the absorbent pad is uncompressed open-cell foam.

27. The applicator of claim 19, wherein the container is collapsible.

28. The applicator of claim 19, wherein the container holds surgical prep solution.

29. The applicator of claim 28, wherein the surgical prep solution comprises iodine.

30. The applicator of claim 19, wherein the container is substantially impermeable to ethylene oxide gas.

31. The applicator of claim 19, wherein the absorbent material is attached to the distributor element by a seal.

32. The applicator of claim 31, wherein the seal comprises a weld such that the pad is mechanically bonded to the distributor element.

33. A method of applying surgical prep solution, the method comprising:
providing the applicator of claim 1, providing surgical prep solution in the container; and dispensing the surgical prep solution.

34. The method of claim 33, wherein the surgical prep solution comprises iodine and the collapsible container is substantially impermeable to ethylene oxide gas before the dispensing.

35. The method of claim 33, wherein the absorbent pad is attached to the distributor element by a seal.

36. The method of claim 35, wherein the seal comprises a weld such that the pad is mechanically bonded to the distributor element.

37. An applicator for dispensing a fluid, comprising:
a hollow elongate member comprising a container;
a flange extending radially outward from said hollow elongate member; and
distributor element attached to the flange, the distributor element comprising:
a first side and a second side;
at least two orifices;
a projecting element comprising a series of interconnecting ribs that form chambers on the first side of the distributor element;
and an absorbent pad attached to the projecting element;
wherein at least a portion the projecting element is proximate the center of the distributor element and separates the at least two orifices such that the at least two orifices are only in fluid communication with each other on the first side of the distributor element through the absorbent pad;
wherein the area of each orifice is significantly smaller than the area of any chamber; and
wherein the projecting element comprises an orifice-free zone that avoids concentrating the fluid in the center of the absorbent pad as the fluid flows through the orifices into the absorbent pad.

* * * * *